United States Patent
Nagy et al.

(10) Patent No.: US 9,894,425 B2
(45) Date of Patent: *Feb. 13, 2018

(54) WIRELESS SENSOR READER

(71) Applicant: Endotronix, Inc., Lisle, IL (US)

(72) Inventors: Michael Nagy, Lombard, IL (US);
Harry D. Rowland, Plainfield, IL (US);
Balamurugan Sundaram, Dunlap, IL (US)

(73) Assignee: ENDOTRONIX, INC., Lisle, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,914

(22) Filed: Nov. 7, 2016

(65) Prior Publication Data
US 2017/0055048 A1 Feb. 23, 2017

Related U.S. Application Data

(63) Continuation of application No. 14/041,738, filed on Sep. 30, 2013, now Pat. No. 9,489,831, which is a
(Continued)

(51) Int. Cl.
*G08C 19/22* (2006.01)
*G05B 23/02* (2006.01)
(Continued)

(52) U.S. Cl.
CPC ............ *H04Q 9/00* (2013.01); *A61B 5/0031* (2013.01); *A61B 5/0215* (2013.01);
(Continued)

(58) Field of Classification Search
None
See application file for complete search history.

(56) References Cited

U.S. PATENT DOCUMENTS 3,872,455 A 3/1975 Fuller et al.
3,888,708 A 6/1975 Wise et al.
(Continued)

FOREIGN PATENT DOCUMENTS

WO WO2005/107583 11/2005
WO WO2006/130488 12/2006
WO WO2012/179008 11/2012

OTHER PUBLICATIONS

The International Bureau of WIPO, International Search Report and Written Opinion of International Searching Authority, Endotronix, Inc., PCT Application No. PCT/US2010/27951, dated Aug. 25, 2010.
(Continued)

*Primary Examiner* — Steven Lim
*Assistant Examiner* — Muhammad Adnan
(74) *Attorney, Agent, or Firm* — McDonald Hopkins LLC

(57) ABSTRACT

A wireless sensor reader is provided to interface with a wireless sensor. The wireless sensor reader transmits an excitation pulse to cause the wireless sensor to generate a ring signal. The wireless sensor reader receives and amplifies the ring signal and sends the signal to a phase-locked loop. A voltage-controlled oscillator in the phase-locked loop locks onto the ring signal frequency and generates a count signal at a frequency related to the ring signal frequency. The voltage-controlled oscillator is placed into a hold mode where the control voltage is maintained constant to allow the count signal frequency to be determined. The reader uses an ambient reading or other information to select a subset of the possible ring signal frequencies, and tunes or adjusts its circuits and algorithms to focus on that subset.

22 Claims, 3 Drawing Sheets

Related U.S. Application Data continuation of application No. 13/455,776, filed on Apr. 25, 2012, now Pat. No. 8,570,186, which is a continuation-in-part of application No. 13/423,693, filed on Mar. 19, 2012, now Pat. No. 8,432,265, which is a continuation of application No. 12/419,326, filed on Apr. 7, 2009, now Pat. No. 8,154,389, which is a continuation-in-part of application No. 12/075,858, filed on Mar. 14, 2008, now abandoned.

(60) Provisional application No. 61/748,647, filed on Apr. 25, 2011, provisional application No. 60/918,164, filed on Mar. 15, 2007.

(51) Int. Cl.
| | | |
|---|---|---|
| *G08B 1/08* | (2006.01) | |
| *G08B 21/00* | (2006.01) | |
| *H04Q 9/00* | (2006.01) | |
| *A61B 5/00* | (2006.01) | |
| *A61B 5/0215* | (2006.01) | |
| *G08C 17/02* | (2006.01) | |

(52) U.S. Cl.
CPC ............ *A61B 5/6882* (2013.01); *G08C 17/02* (2013.01); *A61B 5/7225* (2013.01); *H04Q 2209/47* (2013.01)

(56) References Cited

U.S. PATENT DOCUMENTS

| | | |
|---|---|---|
| 3,943,915 A | 3/1976 | Severson |
| 4,023,562 A | 5/1977 | Hynecek et al. |
| 4,026,276 A | 5/1977 | Chubbuck |
| 4,067,235 A | 1/1978 | Markland et al. |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson et al. |
| 4,511,858 A | 4/1985 | Charavit et al. |
| 4,531,526 A | 7/1985 | Genest |
| 4,567,459 A | 1/1986 | Folger et al. |
| 4,644,420 A | 2/1987 | Buchan |
| 4,651,089 A | 3/1987 | Haigh |
| 4,815,472 A | 3/1989 | Wise et al. |
| 4,881,410 A | 11/1989 | Wise et al. |
| 4,953,387 A | 9/1990 | Johnson et al. |
| 5,005,577 A | 4/1991 | Frenkel |
| 5,006,819 A | 4/1991 | Buchan et al. |
| 5,013,396 A | 5/1991 | Wise et al. |
| 5,046,497 A | 9/1991 | Millar |
| 5,055,838 A | 10/1991 | Wise et al. |
| 5,059,543 A | 10/1991 | Wise et al. |
| 5,108,420 A | 4/1992 | Marks |
| 5,113,868 A | 5/1992 | Wise et al. |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |
| 5,334,952 A | 8/1994 | Maddy et al. |
| 5,343,064 A | 8/1994 | Spangler et al. |
| 5,377,524 A | 1/1995 | Wise et al. |
| 5,417,235 A | 5/1995 | Wise et al. |
| 5,564,434 A | 10/1996 | Halperin et al. |
| 5,581,248 A | 12/1996 | Spillman, Jr. et al. |
| 5,690,674 A | 11/1997 | Diaz |
| 5,920,233 A | 7/1999 | Denny |
| 5,992,769 A | 11/1999 | Wise et al. |
| 6,015,386 A | 1/2000 | Kensey et al. |
| 6,024,704 A * | 2/2000 | Meador ................ A61B 5/0215 128/899 |
| 6,025,725 A | 2/2000 | Gershenfeld et al. |
| 6,109,113 A | 8/2000 | Chavan et al. |
| 6,111,520 A | 8/2000 | Allen et al. |
| 6,126,675 A | 10/2000 | Shchervinsky et al. |
| 6,140,144 A | 10/2000 | Najafi et al. |
| 6,174,322 B1 | 1/2001 | Schneidt |
| 6,190,400 B1 | 2/2001 | Van De Moer et al. |
| 6,206,835 B1 | 3/2001 | Spillman, Jr. et al. |
| 6,232,150 B1 | 5/2001 | Lin et al. |
| 6,278,379 B1 | 8/2001 | Allen et al. |
| 6,287,256 B1 | 9/2001 | Park et al. |
| 6,309,350 B1 | 10/2001 | VanTassel et al. |
| 6,331,163 B1 | 11/2001 | Kaplan |
| 6,338,284 B1 | 1/2002 | Najafi et al. |
| 6,447,449 B1 | 9/2002 | Fleischman et al. |
| 6,454,720 B1 | 9/2002 | Clerc et al. |
| 6,471,656 B1 | 10/2002 | Shalman et al. |
| 6,477,901 B1 | 11/2002 | Tadigadapa et al. |
| 6,499,354 B1 | 12/2002 | Najafi et al. |
| 6,570,457 B2 | 5/2003 | Fischer |
| 6,592,608 B2 | 7/2003 | Fisher et al. |
| 6,636,769 B2 | 10/2003 | Govari et al. |
| 6,645,143 B2 | 11/2003 | VanTassel et al. |
| 6,647,778 B2 | 11/2003 | Sparks |
| 6,658,300 B2 | 12/2003 | Govari et al. |
| 6,666,826 B2 | 12/2003 | Salo et al. |
| 6,667,725 B1 | 12/2003 | Simons et al. |
| 6,680,654 B2 | 1/2004 | Fischer et al. |
| 6,682,490 B2 | 1/2004 | Roy et al. |
| 6,713,828 B1 | 3/2004 | Chavan et al. |
| 6,749,622 B2 | 6/2004 | McGuckin, Jr. et al. |
| 6,764,446 B2 | 7/2004 | Wolinsky et al. |
| 6,779,406 B1 | 8/2004 | Kuznia et al. |
| 6,783,499 B2 | 8/2004 | Schwartz |
| 6,824,521 B2 | 11/2004 | Rich et al. |
| 6,838,640 B2 | 1/2005 | Wise et al. |
| 6,844,213 B2 | 1/2005 | Sparks |
| 6,855,115 B2 | 2/2005 | Fonseca et al. |
| 6,890,300 B2 | 5/2005 | Lloyd et al. |
| 6,893,885 B2 | 5/2005 | Lemmerhirt et al. |
| 6,916,310 B2 | 7/2005 | Sommerich |
| 6,923,625 B2 | 8/2005 | Sparks |
| 6,926,670 B2 | 8/2005 | Rich et al. |
| 6,932,114 B2 | 8/2005 | Sparks |
| 6,935,010 B2 | 8/2005 | Tadigadpa et al. |
| 6,939,299 B1 | 9/2005 | Petersen et al. |
| 6,959,608 B2 | 11/2005 | Bly et al. |
| 6,968,743 B2 | 11/2005 | Rich et al. |
| 6,981,958 B1 | 1/2006 | Gharib et al. |
| 7,001,398 B2 | 2/2006 | Carley et al. |
| 7,004,015 B2 | 2/2006 | Chang-Chien et al. |
| 7,013,734 B2 | 3/2006 | Zdeblick et al. |
| 7,018,337 B2 * | 3/2006 | Hood, Jr. ........... A61B 5/02225 600/490 |
| 7,028,550 B2 | 4/2006 | Zdeblick et al. |
| 7,046,964 B1 | 5/2006 | Sullivan et al. |
| 7,048,756 B2 | 5/2006 | Eggers et al. |
| 7,059,176 B2 | 6/2006 | Sparks |
| 7,059,195 B1 | 6/2006 | Liu et al. |
| 7,066,031 B2 | 6/2006 | Zdeblick et al. |
| 7,073,387 B2 | 7/2006 | Zdeblick et al. |
| 7,081,125 B2 | 7/2006 | Edwards et al. |
| 7,137,953 B2 | 11/2006 | Eigler et al. |
| 7,146,861 B1 | 12/2006 | Cook et al. |
| 7,147,604 B1 | 12/2006 | Allen et al. |
| 7,149,587 B2 | 12/2006 | Wardle et al. |
| 7,162,926 B1 | 1/2007 | Guziak et al. |
| 7,190,937 B1 | 3/2007 | Sullivan et al. |
| 7,192,001 B2 | 3/2007 | Wise et al. |
| 7,198,603 B2 | 4/2007 | Penner et al. |
| 7,211,048 B1 | 5/2007 | Najafi et al. |
| 7,228,735 B2 | 6/2007 | Sparks et al. |
| 7,245,117 B1 | 7/2007 | Joy et al. |
| 7,273,457 B2 | 9/2007 | Penner |
| 7,284,442 B2 | 10/2007 | Fleischman et al. |
| 7,290,454 B2 | 11/2007 | Liu |
| 7,425,200 B2 | 9/2008 | Brockway et al. |
| 7,432,723 B2 | 10/2008 | Ellis et al. |
| 7,466,120 B2 | 12/2008 | Miller et al. |
| 7,483,805 B2 | 1/2009 | Sparks et al. |
| 7,498,799 B2 | 3/2009 | Allen et al. |

(56) References Cited

U.S. PATENT DOCUMENTS

| | | | |
|---|---|---|---|
| 7,550,978 B2 | 6/2009 | Joy et al. | |
| 7,566,308 B2 | 7/2009 | Stahmann | |
| 7,641,619 B2 | 1/2010 | Penner | |
| 7,679,355 B2 | 3/2010 | Allen et al. | |
| 7,839,153 B2 | 11/2010 | Joy et al. | |
| 7,936,174 B2 | 5/2011 | Ellis et al. | |
| 8,154,389 B2 | 4/2012 | Rowland et al. | |
| 8,271,093 B2 * | 9/2012 | Von Arx | A61B 5/0031 607/60 |
| 8,432,265 B2 | 4/2013 | Rowland et al. | |
| 8,493,187 B2 | 7/2013 | Rowland et al. | |
| 8,570,186 B2 | 10/2013 | Nagy et al. | |
| 8,866,788 B1 * | 10/2014 | Birnbaum | G06F 3/016 340/407.2 |
| 9,044,150 B2 * | 6/2015 | Brumback | A61B 5/02433 |
| 9,723,997 B1 * | 8/2017 | Lamego | A61B 5/0205 |
| 2002/0045921 A1 | 4/2002 | Wolinsky et al. | |
| 2002/0072656 A1 | 6/2002 | Vantassel et al. | |
| 2002/0115920 A1 | 8/2002 | Rich et al. | |
| 2002/0138009 A1 | 9/2002 | Brockway et al. | |
| 2002/0151816 A1 | 10/2002 | Rich et al. | |
| 2002/0177782 A1 | 11/2002 | Penner | |
| 2002/0188207 A1 | 12/2002 | Richter | |
| 2003/0062957 A1 | 4/2003 | Terashima et al. | |
| 2003/0136417 A1 | 7/2003 | Fonseca et al. | |
| 2003/0139677 A1 | 7/2003 | Fonseca et al. | |
| 2003/0139771 A1 | 7/2003 | Fisher et al. | |
| 2003/0158584 A1 | 8/2003 | Cates et al. | |
| 2003/0191496 A1 | 10/2003 | Edwards et al. | |
| 2004/0102806 A1 | 5/2004 | Broome et al. | |
| 2004/0158138 A1 | 8/2004 | Kilcoyne et al. | |
| 2004/0220637 A1 | 11/2004 | Zdeblick et al. | |
| 2004/0255643 A1 | 12/2004 | Wise et al. | |
| 2004/0260164 A1 | 12/2004 | Kilcoyne et al. | |
| 2005/0013685 A1 | 1/2005 | Fonseca et al. | |
| 2005/0015014 A1 | 1/2005 | Fonseca et al. | |
| 2005/0043601 A1 | 2/2005 | Kilcoyne et al. | |
| 2005/0049634 A1 | 3/2005 | Chopra | |
| 2005/0080346 A1 | 4/2005 | Gianchandani et al. | |
| 2005/0090719 A1 | 4/2005 | Scheiner et al. | |
| 2005/0103114 A1 | 5/2005 | Bly et al. | |
| 2005/0154321 A1 | 7/2005 | Wolinsky et al. | |
| 2005/0160825 A1 | 7/2005 | Zdeblick et al. | |
| 2005/0160827 A1 | 7/2005 | Zdeblick et al. | |
| 2005/0187482 A1 | 8/2005 | O'Brien et al. | |
| 2005/0228308 A1 | 10/2005 | Iddan et al. | |
| 2005/0288596 A1 | 12/2005 | Eigler et al. | |
| 2005/0288604 A1 | 12/2005 | Eigler et al. | |
| 2005/0288722 A1 | 12/2005 | Eigler et al. | |
| 2006/0047205 A1 | 3/2006 | Ludomirsky et al. | |
| 2006/0052821 A1 | 3/2006 | Abbot et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0116590 A1 | 6/2006 | Fayram et al. | |
| 2006/0122522 A1 | 6/2006 | Chavan et al. | |
| 2006/0129050 A1 | 6/2006 | Martinson et al. | |
| 2006/0161171 A1 | 7/2006 | Schwartz | |
| 2006/0177956 A1 | 8/2006 | O'Brien et al. | |
| 2006/0178583 A1 | 8/2006 | Montegrande et al. | |
| 2006/0178695 A1 | 8/2006 | Decant, Jr. et al. | |
| 2006/0196277 A1 | 9/2006 | Allen et al. | |
| 2006/0206146 A1 | 9/2006 | Tenerz | |
| 2006/0212047 A1 | 9/2006 | Abbot et al. | |
| 2006/0217762 A1 | 9/2006 | Meahs et al. | |
| 2006/0217763 A1 | 9/2006 | Abbot et al. | |
| 2006/0217764 A1 | 9/2006 | Abbot et al. | |
| 2006/0229488 A1 | 10/2006 | Ayre et al. | |
| 2006/0241354 A1 | 10/2006 | Allen | |
| 2006/0244465 A1 | 11/2006 | Kroh et al. | |
| 2006/0271078 A1 | 11/2006 | Modesitt | |
| 2006/0287602 A1 | 12/2006 | O'Brien et al. | |
| 2007/0007240 A1 | 1/2007 | Wise et al. | |
| 2007/0028698 A1 | 2/2007 | Guziak et al. | |
| 2007/0032734 A1 | 2/2007 | Najafi et al. | |
| 2007/0049980 A1 | 3/2007 | Zielinski et al. | |
| 2007/0049984 A1 | 3/2007 | Osypka | |
| 2007/0060959 A1 | 3/2007 | Salo et al. | |
| 2007/0073351 A1 | 3/2007 | Zielinski et al. | |
| 2007/0088388 A1 | 4/2007 | Opolski et al. | |
| 2007/0096715 A1 | 5/2007 | Joy et al. | |
| 2007/0100215 A1 | 5/2007 | Powers et al. | |
| 2007/0106246 A1 | 5/2007 | Modesitt | |
| 2007/0106328 A1 | 5/2007 | Wardle et al. | |
| 2007/0106333 A1 | 5/2007 | Fernandez | |
| 2007/0112358 A1 | 5/2007 | Abbott et al. | |
| 2007/0118039 A1 | 5/2007 | Bodecker et al. | |
| 2007/0149880 A1 | 6/2007 | Willis | |
| 2007/0160748 A1 | 7/2007 | Schugt et al. | |
| 2007/0210786 A1 | 9/2007 | Allen et al. | |
| 2008/0015421 A1 | 1/2008 | Penner | |
| 2009/0115396 A1 | 5/2009 | Allen et al. | |
| 2009/0189741 A1 | 7/2009 | Rowland et al. | |
| 2009/0224773 A1 | 9/2009 | Joy et al. | |
| 2009/0224837 A1 | 9/2009 | Joy et al. | |
| 2010/0026318 A1 | 2/2010 | Kroh et al. | |
| 2010/0161004 A1 | 6/2010 | Najafi et al. | |
| 2010/0308974 A1 | 12/2010 | Rowland et al. | |

OTHER PUBLICATIONS

The International Bureau of WIPO, International Search Report and Written Opinion of International Searching Authority, Nunez, Anthony I., PCT Application No. PCT/US2008/03475, dated Aug. 4, 2008.

Haynes, H.E. & Witchey, A.L., Medical Electronics: The Pill That "Talks", DEP, pp. 52-54, Camden, N.J.

Collins, Carter, Miniature Passive Pressure Transensor for Implanting in the Eye, Transactions on Bio-Medical Engineering, vol. BME-14, No. 2, pp. 74-83, Apr. 1967.

Niagumo, J., Uchiyama, A., Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.

The International Bureau of WIPO, International Search Report and Written Opinion of International Searching Authority, Endotronix, Inc., PCT Application No. PCT/US2012/34979, dated Nov. 2, 2012.

The International Bureau of WIPO, International Search Report and Written Opinion of International Searching Authority, Endotronix, Inc., PCT Application No. PCT/US2009/39730, dated Jun. 30, 2009.

\* cited by examiner

WIRELESS SENSOR READER

CROSS-REFERENCE TO RELATED APPLICATIONS

This application is a continuation of U.S. patent application Ser. No. 14/041,738 entitled "WIRELESS SENSOR READER," filed Sep. 30, 2013 (now U.S. Pat. No. 9,489,831), which claims priority to U.S. patent application Ser. No. 13/455,776 entitled "WIRELESS SENSOR READER," filed on Apr. 25, 2012 (now U.S. Pat. No. 8,570,186), which claims priority to Provisional Patent Application No. 61/478,647 entitled "WIRELESS SENSOR READER TUNING BASED ON AMBIENT CONDITION," filed on Apr. 25, 2011, and which is a continuation-in-part of U.S. patent application Ser. No. 13/423,693 entitled "WIRELESS SENSOR READER," filed on Mar. 19, 2012 (now U.S. Pat. No. 8,432,265), which is a continuation of U.S. patent application Ser. No. 12/419,326 entitled "WIRELESS SENSOR READER," filed on Apr. 7, 2009 (now U.S. Pat. No. 8,154,389), which is a continuation-in-part of U.S. patent application Ser. No. 12/075,858 filed on Mar. 14, 2008, which claims priority to U.S. Provisional Application No. 60/918,164 filed on Mar. 15, 2007 each of which are hereby incorporated by reference in their entirety.

FIELD OF INVENTION

The present invention generally relates to an apparatus and device for measuring a wireless signal from a sensor.

BACKGROUND

Wireless sensor and reader systems may be designed to wirelessly monitor the status of a remote sensor. Some such wireless systems include a sensor that transduces a physical parameter into a signal frequency. A reader is then configured to receive and measure the frequency of the sensor signal.

FIG. 1 illustrates an example of an operational frequency bandwidth of a wireless sensor/reader system and the corresponding parameter. As shown, the corresponding parameter is pressure, however it will be appreciated that the concept described herein may apply to any transduced parameter. The exemplary frequency range of the illustrated wireless sensor is from 13 to 14 MHz, which corresponds to absolute pressures of 550-900 mmHg. In the example shown in FIG. 1, frequency is inversely proportional to pressure.

In wireless sensor/reader systems, the sensor may be stimulated by a transmit pulse from a reader, causing the sensor to emit a ring back or "ring" signal at its resonant frequency once that stimulus is removed. The reader may measure the frequency of the ring signal and use a calibration table or formula to determine the sensed pressure.

The ring signal, as received at the reader, may be low power and may decay very quickly, particularly if the distance between sensor and reader is great. This is a problem with all similar wireless sensor systems, whether the systems utilizes a transmit signal that is fixed or swept. Other types of wireless sensor systems, such as those based on grid-dip techniques, may require a relatively long time and many transmit cycles to identify the sensor's resonance frequency, especially when the possible range of resonance frequencies is large.

Some wireless reader/sensor system designs require a gauge pressure reading, meaning pressure relative to local atmospheric pressure. In such designs, however, the sensor is often located at a position where it cannot access atmospheric pressure and thus cannot directly deliver a gauge pressure reading. For example, a blood pressure sensor implanted in the pulmonary artery is not capable of directly accessing atmospheric pressure. To deal with certain medical conditions, clinicians typically wish to know the gauge pressure of the pulmonary artery across a range of 100 mmHg. However, the implanted sensor has no way of knowing what the local atmospheric pressure is. In other words, the implanted sensor is only capable of sensing absolute pressure.

One solution is to place an ambient pressure sensor in the reader. The reader then measures absolute pressure from the implanted sensor, as well as absolute atmospheric ambient pressure from its ambient pressure sensor, and subtracts the ambient pressure from the absolute pressure to obtain gauge pressure.

The example in FIG. 1 illustrates a pressure range between 550-900 mmHg absolute. Ambient pressures in the inhabited regions of earth typically range from 550-800 mmHg absolute. Thus, to measure 0-100 mmHg gage, a sensor's absolute range must go from 550 mmHg (lowest ambient 550 mmHg plus lowest gauge 0 mmHg) to 900 mmHg (highest ambient 850 mmHg plus highest gauge 100 mmHg).

Therefore, there is a need to measure the frequency of a weak signal where the signal's full scale range is wide, but where only a small subset of that full range is used for any individual measurement.

Regardless of the method used to determine the sensor signal frequency, various circuits within the reader must be adapted or tuned to capture the maximum amount of energy in the sensor signal without capturing unwanted energy from sources other than the sensor, such as natural or man-made noise. For example, the reader's receiver antenna and internal filters, such as analog or digital filters, may be tuned to a passband that passes any possible frequency at which the sensor might resonate and rejects all frequencies outside that passband. However, widening the passbands of antennas and filters can cause problems, including higher attenuation, lower signal-to-noise ratios, and increased susceptibility to unwanted interfering signals.

Fixed frequency systems have difficulty overcoming these problems. Some swept frequency systems may attempt to overcome the problems by constantly re-tuning the receivers and filters to match the instantaneous frequency being transmitted. This, however, usually requires significant additional circuitry and processing.

Therefore, an improved method and apparatus are needed.

SUMMARY

A reader device is provided to interface with a wireless sensor. The reader emits a short pulse of energy or a short burst of radio frequency energy to cause the wireless sensor to ring. Immediately after the transmission, the reader receives and amplifies the sensor signal, then sends the signal to a phase-locked loop ("PLL") that locks to the sensor ring frequency. Once the PLL has locked to the ring frequency, the PLL's voltage controlled oscillator ("VCO") is placed in a hold mode to maintain the VCO frequency at the locked frequency. The VCO frequency is counted to determine the sensor resonant frequency.

The reader may include a device, such as a second sensor, to determine a set of possible frequency values of the ring signal. The components of the reader device may be tuned to the set of possible frequency values that are identified.

BRIEF DESCRIPTION OF THE DRAWINGS

Objects and advantages together with the operation of the invention may be better understood by reference to the detailed description taken in connection with the following illustrations, wherein.

DETAILED DESCRIPTION

Figure 1:
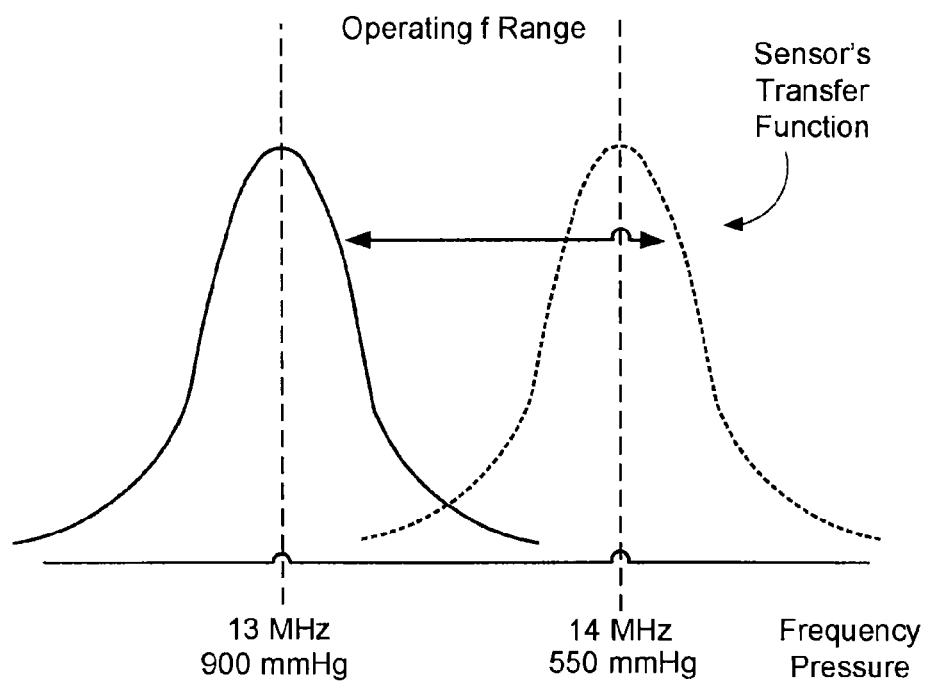
FIG. 1 is a graph of an operational frequency bandwidth of a sensor and corresponding parameter.
Figure 2:
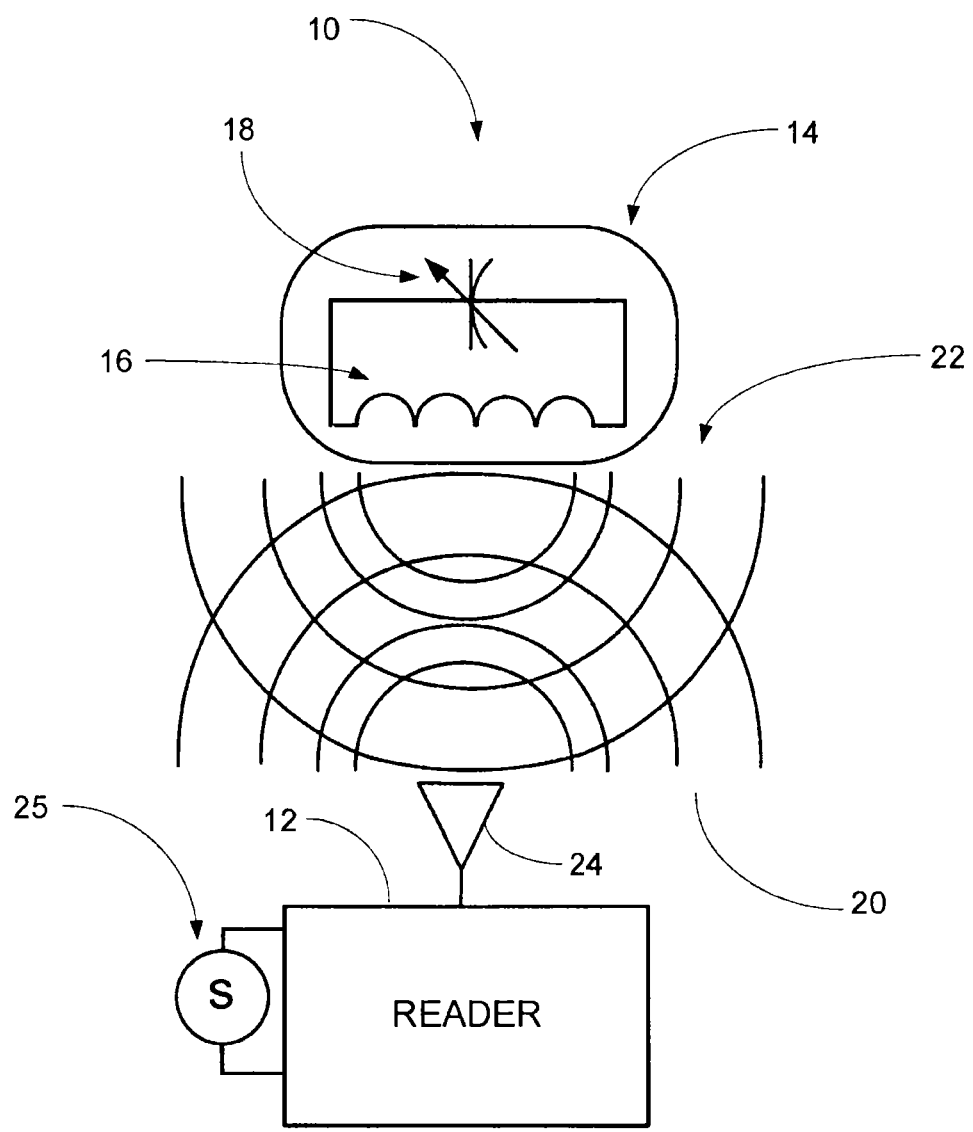
FIG. 2 is an embodiment of a wireless sensor system.

Reference will now be made in detail to exemplary embodiments of the present invention, examples of which are illustrated in the accompanying drawings. It is to be understood that other embodiments may be utilized and structural and functional changes may be made without departing from the respective scope of the present invention.

A wireless system 10 is generally provided. The wireless system 10 may include a wireless reader 12 and a wireless sensor 14. The wireless sensor 14 may be a passive device, such as a device comprising a capacitor 16 and an inductor 18, or an active device. The wireless sensor 14 may be implantable, such as implantable into a living being. For example, the wireless sensor 14 may be implanted in a human body to monitor a condition or parameter within the human body.

The reader 12 may be configured to transmit an excitation pulse 20 to excite the sensor 14. The excitation pulse 20 may cause the sensor 14 to ring or emit a ring signal 22 at its resonant frequency. The resonant frequency of the sensor 14 may vary based on a parameter sensed by the sensor 14. The reader 12 may measure the frequency of the ring signal 22 and determine the sensed parameter. For example, the reader 12 may utilize a formula, lookup table or calibration table to determine the sensed parameter.

The reader 12 may include a receiver to receive the ring signal 22 from the sensor 14. The receiver may comprise an antenna 24 or any other signal receiving device. The receiver may further include one or more filters, such as for example analog or digital filters, to filter the signal 22 received from the sensor 14. The filters may be tuned to a passband to allow a desired frequency bandwidth to be received by the reader 12. The passband may be narrowed to pass only a frequency band that corresponds to a specific parametric range of interest 26, shown in FIG. 3.

Exemplary embodiments described herein may make reference to monitoring and sensing a specific parameter, such as pressure. It will be appreciated, however, that the systems and methods set forth herein may be applied to any measured or sensed parameter, such as pressure, temperature, or any other parameter.

Figure 3:
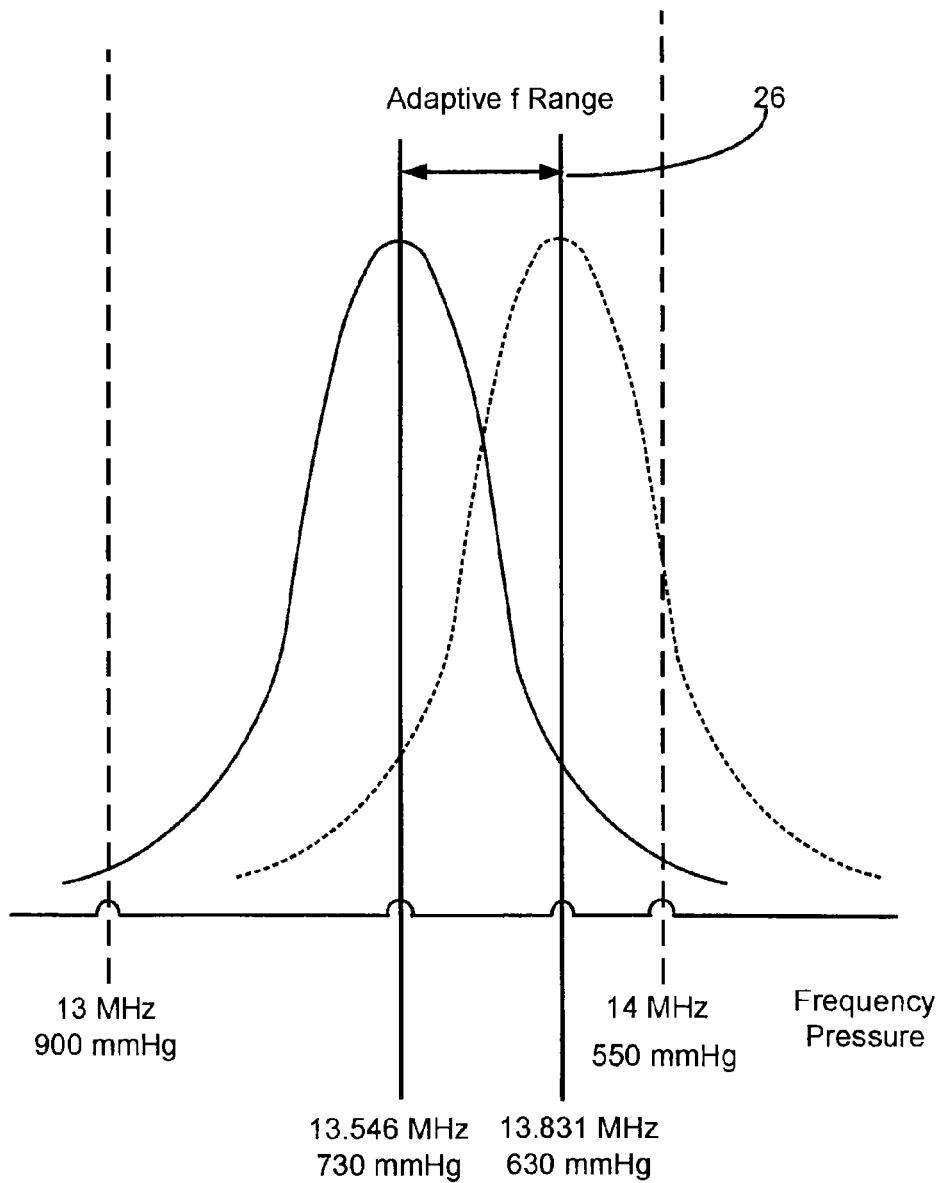
FIG. 3 is a graph of an operational frequency bandwidth of a sensor and corresponding parameter and bandpass window.

By way of a non-limiting example, a wireless system 10 adapted to sense a pressure, such as blood pressure, may include filters to narrow the passband window 26 to only receive frequencies that correspond to pressures within a 100 mmHg gauge pressure range. An example of this passband range 26 is illustrated in FIG. 3. The frequencies that correspond to pressures within a 100 mmHg gauge pressure range may be a "passband window" or "window of interest" 26 of the frequencies that provide the optimal or most valuable data. It will be appreciated, however, that the passband window 26 may correspond to any appropriate range of the sensed parameter.

The spectral location of the passband window 26 within the total range of absolute pressure may vary to capture the desired data. For example, the location of the window 26 may be determined based on the ambient pressure at the time the reader 12 is receiving the ring signal 22 from the sensor 14. To that end, the reader 12 may include an ambient sensor 25, such as an ambient pressure sensor, to sense an ambient condition, such as pressure. The ambient sensor 25 may be embedded in or located on the reader 12. The ambient sensor 25 may also be located away from the reader 12, such as part of another device or system that communicates its ambient reading to the reader 12 or to a third party processor, for determining the location of the passband window 26.

As shown in the graph illustrated in FIG. 3, the passband window 26 may be optimally located based on the ambient pressure measured by the reader's ambient pressure sensor 25. For example, in an embodiment where the sensor is a wireless pressure sensor implanted in the pulmonary artery of a human being, the pressure range of interest is 0-100 mmHg above ambient. Therefore, the Reader's processor would be programmed to locate a passband window 26 such that its edges are at frequencies corresponding to the ambient pressure reading, and a pressure that is 100 mmHg greater than the ambient pressure reading, as shown in FIG. 3. Accordingly, the reader 12 may tune its antenna 24, as well as its internal circuits and algorithms, to focus the passband window 26 near the ambient pressure.

In an embodiment, a wireless sensor 14 may be implanted into a human being located at relatively high altitude, for example an altitude having an ambient pressure near 630 mmHg absolute. The pressure range of interest may therefore be 630-730 mmHg absolute, corresponding to a frequency passband window 26 of 13.831-13.546 MHz. The reader 12 may measure the ambient pressure using its ambient pressure sensor 25. The reader 12 may then determine, from the ambient pressure measurement, the subset of the full-scale frequency range that will contain the remote sensor's frequency. The reader 12 may then tune its receiver, such as the antennas 24, filters, amplifiers, other circuits, or algorithms, to pass the desired subset and block the unwanted portion of the range. For example, the reader 12 may increase the Q of its receiving antenna by narrowing its bandwidth to match the frequency window 26. Additionally, the reader 12 may increase the gain and signal-to-noise ratio of one or more amplifiers in the receive chain by tuning them to the passband window 26. The reader 12 may also tune filters in the receive chain to match the passband window 26, and thus filter out any noise or interference outside the passband window 26. The reader 12 may take numerous pressure readings from the sensor and average them (in its own embedded processor or in a remote processor) to further improve accuracy. The averaging processor may implement an algorithm by which all readings that fall outside the passband window 26 are considered spurious outliers and are not included in the average.

This system and method, as described, provide several advantages over known systems and methods. For example, restricting the passband window 26 of the received ring signal 22 may allow a sensor 14 with a higher Q to be used, thus providing a longer decay time and higher ring signal 22 amplitude. Restricting the passband window 26 also allows for receiver antennas 24 and filters having a higher Q to be used, thus increasing signal to noise ratio. Further, in systems that utilize a fixed-frequency excitation pulse 20, the sensor's transfer function roll-off dictates that the ring signal 22 may be weaker when the sensor 14 is near the edges of its operational frequency range. Adapting the reader's circuitry to focus on bands near the edges may compensate for this effect.

Once the passband window 26 has been determined, many of the reader's internal components may be tuned to focus only on the range of the passband window 26. For example, the reader's receive antenna 24 may be tuned to the passband window 26 containing the ring signal 22. This may be accomplished by switching reactive components in and out of the antenna circuit, including parts of the antenna 24, or by other methods known in the art.

The wireless system 10 may include an amplifier section. The amplifier section may include filters and amplifiers. The filters and amplifiers may be adaptively tuned to the frequency passband window 26 that contains the ring signal 22. This can be accomplished by switching reactive components in and out of the amplifier and filter circuits, or by other methods known in the art.

The wireless system 10 may include at least one phase lock loop (PLL) to lock onto and help determine the ring frequency. The initial reference frequency for the PLL may be set to approximately the center of the frequency passband window 26. This will reduce the time it takes for the PLL to lock onto the ring signal 22 frequency. For example, the reader 12 processor may calculate or look up the control voltage of the PLL's voltage controlled oscillator (VCO) that corresponds to the center of the passband window 26, as defined by the reader's ambient pressure sensor 25. Other methods and circuits for locking and pre-locking the PLL may be used in conjunction with the systems and methods described herein.

The excitation pulse 20 emitted by the reader 12 may be held at an approximately fixed frequency. The fixed excitation pulse 20 may be adapted to be located near the center of the passband window 26 containing the ring signal 22. As a result, the system may utilize a sensor 14 having a higher Q that may provide a stronger, longer lasting ring signal 22.

The wireless system 10 may utilize a swept frequency excitation pulse 20. The bandwidth of the swept frequency excitation pulse 20 may be limited to the passband window 26 containing the ring signal 22. Limiting the excitation pulse 20 in this manner may reduce the time required to acquire the ring signal 22 and allow more samples to be taken for a given pressure instance.

The parameter measured by the sensor 14 may be static or quasi-static in comparison to the speed of measurement. By way of a non-limiting example, a measured blood pressure waveform may be static or quasi-static in comparison to the speed of measurement. In such circumstances, the reader 12 may take multiple readings of the sensor 14 measurement and average them using a processing algorithm. For example, as the ring signal 22 gets weaker and the signal-to-noise ratio (SNR) decreases, the number of noisy, spurious readings may increase. The reader 12 may be configured to ignore any measurements that lie outside the passband window 26 during the averaging process to remove outlying and inaccurate data.

The reader 12 may sample the incoming ring signal 22 and compare the input data with the passband window 26. Based on the comparison, the input data from the ring signal 22 may be stored or discarded. The reader 12 may also optimize or enhance processing of the signal, for example with FFT methods, by only processing portions of the signal that are within the allowed frequency band based on the filtered passband window 26. Other methods of improving the measurement of the received signal based on narrowing the allowed frequency band to match the ambient measurement may also be utilized.

The examples used herein are directed to an ambient pressure reading to determine a narrowed bandwidth for the absolute reading and adapt the reader 12 circuitry and/or algorithms to that bandwidth. It will be appreciated, however, that this method may be used in any circumstance where two sensor measurements are taken and the result of one measurement can be used to limit the possible outcomes of the other measurement. The sensed parameter is not limited to pressure but may be any parameter. Further, the wireless sensors 14 and ambient sensor do not necessarily have to measure the same quantity or parameter but may instead measure different quantities or parameters.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

We claim:

1. A wireless sensor reader comprising:
   an antenna for transmitting a plurality of excitation pulses to a wireless sensor;
   at least one receiver for receiving a ring signal from said wireless sensor in response to said excitation pulses, said receiver including at least one filter to filter said ring signal received from said wireless sensor,
   wherein said filter defines a passband window to allow a frequency bandwidth to be received by the reader,
   wherein said passband window may be defined to pass only a frequency band that corresponds to a parametric range, and
   wherein an ambient pressure sensor is in communication with said filter to at least partially define the passband window of a resonant frequency value to optimize itself for operation based on said passband window.

2. The wireless sensor reader of claim 1, wherein the ambient pressure sensor is located on the wireless sensor reader.

3. The wireless sensor reader of claim 1, wherein the parametric range is within a 100 mmHg gauge pressure range.

4. The wireless sensor reader of claim 1 wherein said antenna is also configured to receive said ring signal from said wireless sensor.

5. The wireless sensor reader of claim 1, wherein said wireless sensor is configured to change its resonant frequency in proportion to at least one sensed parameter.

6. The wireless sensor reader of claim 1, wherein the antenna and the receiver are tuned to the passband window wherein signals having a frequency outside of the passband window are blocked from the receiver.

7. The wireless sensor reader of claim 1, wherein the reader takes a plurality of readings from the wireless sensor and averages the readings to improve accuracy.

8. The wireless sensor reader of claim 7, wherein the reader is configured to ignore readings that lie outside the passband window during the averaging process.

9. The wireless sensor reader of claim 1, further comprising at least one amplifier that is adaptively tuned to the passband window.

10. The wireless sensor reader of claim 1, further comprising at least one phase lock loop that is adaptively tuned to the passband window.

11. The wireless sensor reader of claim 1, wherein the plurality of excitation pulses are emitted at a fixed frequency that is adapted to be located near the center of the passband window.

12. A wireless sensor reader comprising:
a transmit circuit configured to generate an excitation pulse to cause a wireless sensor to emit a ring signal;
an antenna configured to transmit said excitation pulse and receive said ring signal;
a phase-locked loop circuit configured to receive said ring signal, said phase-locked loop circuit including a voltage-controlled oscillator configured to generate a count signal at a frequency related to said ring signal frequency;
a circuit for identifying a set of possible frequency values of said ring signal for an individual reading;
wherein said phase-locked loop circuit is capable of being placed in a sample mode to receive said ring signal and adjust the frequency of said count signal based on the frequency of said ring signal;
wherein at least one of said transmit circuit, said phase-locked loop circuit,
said antenna, and said voltage-controlled oscillator is tunable to the identified set of possible frequency values; and
wherein said circuit defines a passband window to allow a frequency bandwidth to be received by the reader, and wherein the passband window may be defined to pass only a frequency band that corresponds to a parametric range.

13. The wireless sensor reader of claim 12, wherein said circuit for identifying said set of possible frequency values is a second sensor that measures a parameter related to the parameter being measured by said wireless sensor.

14. The wireless sensor reader of claim 13, wherein said second sensor is an ambient pressure sensor and said wireless sensor is a blood pressure sensor.

15. The wireless sensor reader of claim 12, wherein said antenna is capable of being tuned to transmit an excitation pulse having a frequency that is selected based on said set of possible frequency values of said ring signal.

16. The wireless sensor reader of claim 12, wherein said antenna is capable of being tuned to receive frequencies in a passband based on said set of possible frequency values.

17. The wireless sensor reader of claim 12, wherein said circuitry for conditioning said received signal comprises filters capable of being tuned to reject frequencies outside of a passband based on said set of possible frequency values.

18. The wireless sensor reader of claim 17, wherein said filters comprise digital conversion circuitry and digital filters.

19. The wireless sensor reader of claim 18, wherein said digital filters comprise averaging a set of discrete samples.

20. The wireless sensor reader of claim 12 further comprising a circuitry for conditioning said received signal, wherein said circuitry for conditioning said received signal includes amplifiers capable of being tuned to reject frequencies outside of a passband based on said subset of said ring signal frequency's possible values.

21. The wireless sensor reader of claim 12, wherein said voltage-controlled oscillator's initial frequency value is selected based on said set of possible frequency values of said ring signal.

22. The wireless sensor reader of claim 1, wherein the circuit for identifying a set of possible frequency values of said ring signal includes an algorithm.

* * * * *